(12) United States Patent
Lykke

(10) Patent No.: US 7,259,190 B2
(45) Date of Patent: Aug. 21, 2007

(54) ADHESIVE COMPOSITION

(75) Inventor: Mads Lykke, Bronshoej (DK)

(73) Assignee: Coloplast A/S, Humlebaek (DK)

( * ) Notice: Subject to any disclaimer, the term of this patent is extended or adjusted under 35 U.S.C. 154(b) by 0 days.

(21) Appl. No.: 10/467,058

(22) PCT Filed: Feb. 21, 2002

(86) PCT No.: PCT/DK02/00116

§ 371 (c)(1),
(2), (4) Date: Aug. 18, 2003

(87) PCT Pub. No.: WO02/066087

PCT Pub. Date: Aug. 29, 2002

(65) Prior Publication Data

US 2004/0065232 A1    Apr. 8, 2004

(30) Foreign Application Priority Data

Feb. 21, 2001    (DE)    .................... PA 2001 00289

(51) Int. Cl.
*C09J 11/08*    (2006.01)
*A61L 15/58*    (2006.01)

(52) U.S. Cl. .................. 521/146; 521/148; 521/84.1; 521/96; 521/98; 524/284

(58) Field of Classification Search .......... 525/96, 525/98; 521/50, 84.1, 146, 148, 96, 98; 524/284
See application file for complete search history.

(56) References Cited

U.S. PATENT DOCUMENTS

| 3,339,546 A | | 9/1967 | Chen ............................ 128/156 |
| 4,052,353 A | * | 10/1977 | Scanley ........................ 524/801 |
| 4,059,466 A | * | 11/1977 | Scholl et al. .................. 156/78 |
| 4,367,732 A | | 1/1983 | Poulsen et al. .............. 128/156 |
| 5,547,745 A | * | 8/1996 | Hansen et al. ............... 442/417 |
| 5,674,561 A | | 10/1997 | Dietz et al. ............... 427/208.4 |

FOREIGN PATENT DOCUMENTS

| CA | 2200229 | | 3/1996 |
| CA | 2356925 | * | 6/2000 |
| DE | 44 34 171 | | 3/1996 |
| EP | 0 528 191 | | 2/1993 |
| EP | 1 013 291 | | 6/2000 |
| WO | 91/09633 | | 7/1991 |
| WO | 99/29273 | | 6/1999 |

* cited by examiner

*Primary Examiner*—Irina S. Zemel
(74) *Attorney, Agent, or Firm*—Jacobson Holman PLLC

(57) ABSTRACT

An adhesive composition comprising a polymeric matrix and absorbent particles wherein at least a part of the absorbent particles are microcolloid particles. The microcolloid particles are water absorbent particles preferably having a rounded or spherical shape. The addition of microcolloids to an adhesive provides an improved moisture handling properties compared to state of the art technology as well as the rheological properties of the adhesive matrix may be less affected than by addition of traditional hydrocolloids.

4 Claims, 1 Drawing Sheet

ADHESIVE COMPOSITION

This is a nationalization of PCT/DK02/00116 filed Feb. 21, 2002 and published in English.

FIELD OF THE INVENTION

The present invention relates to adhesive compositions, the process for their preparation and medical devices including such.

BACKGROUND OF THE INVENTION

In medical devices, such as wound dressings and ostomy appliances, it is often desired that the device is moisture absorbing and vapour permeable. These devices often comprise a moisture absorbing adhesive coated on a backing layer. Much effort has been made to optimise the moisture absorbing and moisture transporting properties of the construction.

The use of hydrodolloids as absorbers in matrices such as adhesives are well-known in medical devices. The hydrocolloids have superior properties when it comes to absorption of aqueous liquids. Hydrocolloids are e.g. incorporated into absorbent articles such as sanitary napkins, in wound dressings and in ostomy appliances. In U.S. Pat. No. 3,339,546 a bonding composition of polyisobutylene and hydrocolloids is disclosed. Similarly adhesive compositions based on block copolymers are disclosed in U.S. Pat. No. 4,367,732. The adhesives are intended to be used on the skin or the mucosa.

When incorporated into adhesive, hydrocolloids in the form of particles are preferred. Traditionally, hydrocolloids may be any type of water soluble or swellable material. Both natural polymers or derivatives thereof like carboxy methyl cellulose (CMC), pectin and guar gum, and synthetic polymers like polyacrylic acid and polyvinyl pyrilidone (PVP) may be used.

The physical form of hydrocolloids are relatively coarse and irregular particles, typically about 60-100 µm. The traditional hydrocolloids are hence fairly easy to produce by conventional techniques like milling and their coarse size support safe handling in production, by minimising dust formation.

Adhesives with hydrocolloid particles incorporated are well-known in the art e.g. from International Patent Application No. WO 91/09633 which discloses an adhesive composite comprising a swollen hydrocolloid dispersed in a pressure sensitive adhesive matrix. The swollen hydrocolloids are in the form of irregular particles of different shapes. As the hydrocolloid is swollen, the absorbent capacity of the adhesive composite will be limited.

Usually, the hydrocolloid particles are in a dry, non-swollen state when incorporated in the adhesive matrix.

When hydrocolloid particles are incorporated into adhesives, the properties of the resulting adhesives change. Typically the hardness of the adhesive will increase with the addition of hydrocolloid. This is often undesired in medical devices as it is preferred to have soft and skin-friendly adhesives being capable of following the movements of the skin. Furthermore, it is a disadvantage that the processing of the adhesive will be more difficult when working with hydrocolloid-containing adhesives. Due to the increased hardness of the adhesive the tackiness of the adhesive matrix decrease and may prior to addition of hydrocolloids need to be increased by increasing the adhesiveness of the composition, enhancing the risk of damaging the skin when the device is removed.

When a hydrocolloid containing adhesive is used in medical devices, such as wound dressings or ostomy appliances, the hydrocolloids will also serve as moisture transport from the skin or a wound through to the top the device. In order to optimise the moisture transporting properties of the device a very permeable backing layer is normally used. However, a limiting factor in the moisture transport is often related to the interface between the film and the hydrocolloid particles of the adhesive. To achieve an adhesive with moisture transporting properties, an amount of at least 25% w/w hydrocolloids is needed.

From European Patent Application No. 528 191 is disclosed an adhesive composition comprising hydrocolloids. The particle size of the hydrocolloid is between 1-1000 microns, but preferably an average of 50 microns or less. This size is obtained by pulverising the hydrocolloid, and the resulting powder was then sieved to obtain an average particle size of 50 microns or less. Particles obtained by milling or pulverising will be irregular and sharp-edged, and furthermore, handling of very fine particles may be difficult due to dust problems.

DE Patent Application No. 44 34 171 discloses an absorbent adhesive with absorbent particles incorporated. The particle size is between 10 and 1000 microns, or at least smaller than the thickness of the adhesive layer.

The size of the hydrocolloid particles may be a limiting factor on the thickness of adhesive coatings, as the thickness of the coating cannot be smaller than two to three times the particle size. Very thin coatings may be desired in order to achieve a more flexible product as well as the breathability of the product may be enhanced.

Thus, there is still a need for a skin-friendly adhesive composition being capable of absorbing and transporting moisture, having a good tack, being easy to separate and process.

It has surprisingly been shown that by replacing at least a part of the absorbent particles of the adhesive composition with microcolloid particles, improved properties of the adhesive are achieved.

BRIEF DESCRIPTION OF THE INVENTION

The invention relates to adhesive compositions comprising a polymeric matrix and absorbent particles.

The invention further relates to a medical device comprising an adhesive composition comprising a polymeric matrix and absorbent particles.

The invention also relates to a process for preparing an adhesive composition comprising a polymeric matrix and absorbent particles.

BRIEF DESCRIPTION OF THE DRAWING

The invention is explained more in detail with reference to the drawing in which.

DETAILED DESCRIPTION OF THE INVENTION

Figure 1:
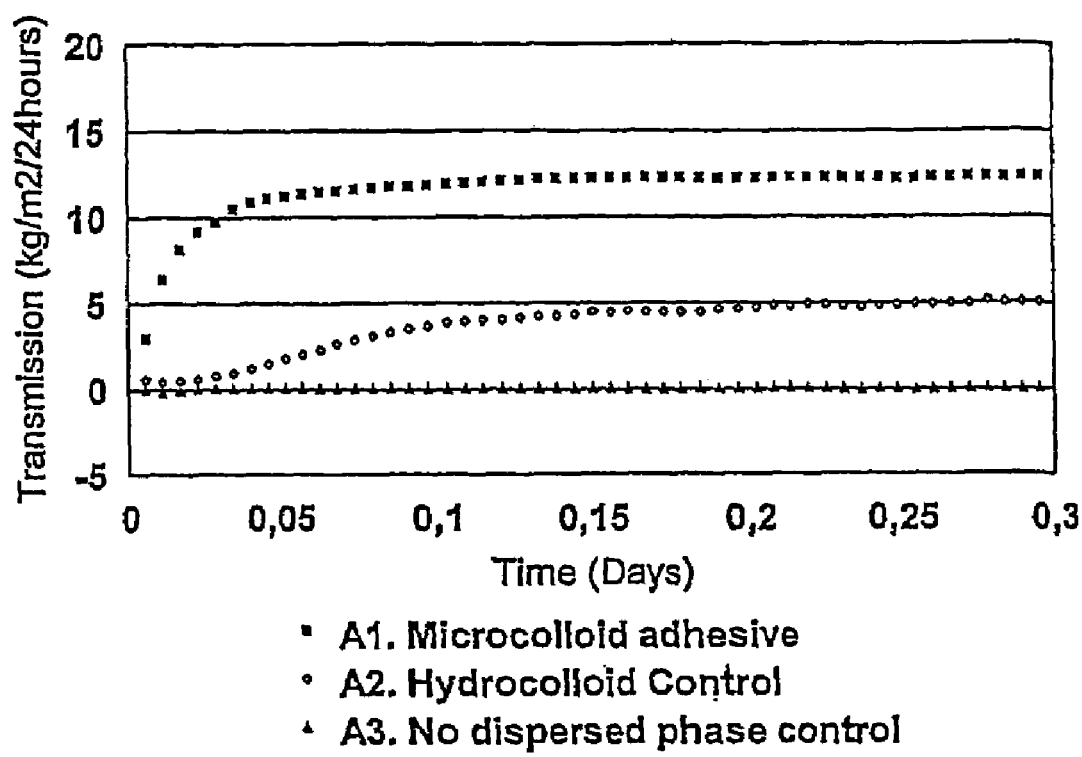
FIG. 1 shows the moisture transmission over time of adhesive compositions.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

The invention relates to an adhesive composition comprising a polymeric matrix and absorbent particles wherein at least a part of the absorbent particles are microcolloid particles having a substantially rounded or spherical shape.

In the adhesive composition of the present invention at least a part of the absorbent particles is present in a finely divided state, for instance as micronised particles of size less than 20 μm, hereafter named microcolloids. It has surprisingly been found that by embedding microcolloids in an adhesive the adhesive composition will achieve reduced hardness and increased moisture transport properties compared to hydrocolloid adhesives. It has additionally been found that the compositions of the present invention are more sturdy to variations in production methods than traditional compositions and lead to reduced viscosity in for instance hot melts.

The microcolloid particles may have a particle size of less than 20 microns.

The microcolloid particles may preferably have a particle size of less than 10 microns.

The microcolloid particles may more preferred have a particle size of less than 6 microns.

The microcolloid particles may most preferred have a particle size of less than 2 microns.

In one embodiment of the invention the microcolloid particles have a particle size of less than 1,5 microns, more preferred less than 1 micron.

The invention relates further to an adhesive composition consisting essentially of a polymeric matrix and absorbent particles wherein at least a part of the absorbent particles are microcolloid particles having a particle size of less than 20 microns.

Depending on the method of preparation, the particle size of the microcolloid particles will normally follow a normal distribution curve, meaning the majority of the particles are having essentially the same size, but a minor part of the particles will be smaller or larger.

In the adhesive composition according to the invention it is preferred that 5-100% w/w, more preferred 10-100% w/w, even more preferred 25-100% w/w and most preferred 50-100% w/w of the absorbent particles are microcolloid particles.

It is preferred that at least 75%, more preferred 90% and most preferred 95% of the microcolloid particles have a particle size below 20 μm, more preferably below 10 μm and even more preferably below 6 μm, and most preferred below 2 μm.

A predominant share of the absorbent particles of the composition of the invention may be microcolloid particles. In one embodiment of the invention 100% of the absorbent particles are microcolloid particles.

Absorbent particles for incorporation into adhesives are often hydrocolloid particles.

The physical form of hydrocolloids used today are relative coarse and irregular particles, typically about 60-100 μm and in the form of a dry powder. These are fairly easy to produce by conventional techniques like milling and the relative coarse particle size makes it possible to handle them at production scale without serious dust problems.

When handling hydrocolloid particles with a substantial amount of fine particles, a powderous formulae will often give rise to dust problems, as well as it will be difficult and explosive to produce particles of such a size by the traditional methods, due to dust and handling problems. Furthermore, particles of a size of less than 20 microns may be inhaled into the lungs and may cause health hazards. Hence, such powders are not commercially available. The microcolloid particles of the composition according to the invention may be prepared e.g. by milling, but will preferably be prepared by an emulsion process, and will be delivered in a carrier liquid in the form of a paste or a liquid suspension, or the micronised particles may be agglomerated into granules or potentially in a free flowing powderous form.

The microcolloid particles may preferably have a substantially rounded or spherical shape. A special advantage of such particles is that they often may be closer packed providing high bulk density, as well as the rounded shape may influence the viscosity and processability of the adhesive.

The microcolloid particles may have a homogeneous, essentially monodisperse size distribution.

The invention further relates to an adhesive composition comprising a polymeric matrix and absorbent particles wherein at least a part of the absorbent particles are in the form of microcolloid particles wherein the microcolloid particles are in a stabilised form.

Preferably, the microcolloids are stabilised by low-molecular weight surfactants.

The polymeric matrix may be a continuous phase and the polymeric matrix may preferably be hydrophobic.

In one embodiment of the invention the polymeric matrix may be hydrophilic.

The polymeric matrix may preferably be a skin-friendly adhesive, optionally an adhesive for medical use.

The invention also relates to a medical device comprising a composition comprising a polymeric matrix and absorbent particles wherein at least a part of the absorbent particles are microcolloids having a substantially rounded or spherical shape.

The smaller size and/or the rounded shape of the microcolloid particles in the composition of the invention may influence the Theological properties of the invention. The viscosity and processing temperature will be lower than when using traditionally sized hydrocolloides, rendering it possible to prepare thinner coatings, e.g. adhesives with a thickness of less than 50 μm, and bevelling of the edge of a thick adhesive as well as the adhesive as such may be easier to mould. The tack of the adhesive may also enhance, due to the softer properties of the adhesive.

Due to their smaller size and preferably rounded shapes the microcolloids and adhesives based on those are able to pass through narrow nozzles, dies and valves. This separates the microcolloids and microcolloid based adhesives from hydrocolloids and hydrocolloid based adhesives, that will block the nozzles, dies and valves or at least increase the viscosity of the adhesives to levels beyond normal processing temperatures. The increase in viscosity combined with possible blocking of narrow nozzles, dies and valves renders the use of standard hydrocolloid based adhesives difficult or impossible in equipment for application of the adhesives in very thin layers by coating with slot dies, spray, swirl, controlled coat or melt-blowing dies and equipment as supplied by companies as Nordson or Rubatech.

Microcolloid based adhesives can be applied to different substrates in very thin open networks, the networks comprises of very thin adhesive strings overlapping each other forming a random open networks of adhesive on the substrate. With this technology it is possible to coat substrates with very open network structures of adhesive and obtain very low, but still sufficiently adhesive, coating weights.

The open and thin networks of adhesives can be produced by a variety of technologies such as spraying the adhesives as particles or pieces of adhesive onto the surface of the substrate thereby creating an open layer of adhesive on the substrate surface. The adhesive may also be applied in thin strings, which are pressed through small holes in dies. The adhesive string can be applied as both parallel lines of adhesive, vibrated strings forming an open random coating such as the ones created by the Controlled coat dies from Nordson, and as overlapping circles creating an open network of adhesive on the substrate. The later can be produced by the swirl dies from Nordson or Rubatech.

The microcolloid based adhesives can also be applied as a random network of very thin pieces of adhesive fibres such a pattern can be created by turning up the airflow on a standard die for swirling adhesive strings the power of the increased airflow tears the adhesive string and dispense it as short thin overlapping adhesive fibres on the substrate thus creating a random open network-structure of adhesive.

Hydrocolloid based adhesives cannot be applied by the methods mentioned above, or at least not as thin coatings as the microcolloid based adhesives. The nozzles, dies and valves used in these processes have very small holes which will be blocked by the large hydrocolloid particles or the significant rise in viscosity created by incorporating the hydrocolloids.

Dies and nozzles with larger holes can of course be constructed and used but this will result in much thicker adhesive strings which again may render it difficult to obtain the very small coating weights. Furthermore, the thick strings may feel both uncomfortable upon direct skin contact and be displeasing to the eye.

Very thin coatings of microcolloid based adhesives may also be obtained with coating by the use of slot dies. Normally the thickness of the adhesive containing standard size hydrocolloids is limited by the size of these particles. The adhesive layer can only be as thin as the largest of the hydrocolloid particles and not even that if a smooth surface of the coating is to be achieved.

With microcolloid based adhesives coatings much thinner than the particle size of hydrocolloids may be achieved. Furthermore, it has been shown that when very thin layers of microcolloid based adhesives are coated with slot dies on porous substrates such as a foam, e.g. polyurethane foam, a porous adhesive film is achieved due to the thin adhesive film rupturing over the pores.

This opens up the possibility of creating porous adhesive coatings on porous substrates with slot dies. Porous coatings from slot dies opens up a range of new possibilities because slot dies offers very good control over the thickness of the adhesive layer and the amount of adhesive that is deposited on the substrate.

The porous character of the adhesive coating on porous substrates allows fluids such as wound exudates to pass through the layer quickly. The adhesive layer may thus serve as a wound contact layer.

The microcolloid based adhesives renders it possible to produce a highly absorbent and permeable adhesive that can be coated in open networks for even higher permeability to be achieved or for reducing the amount of adhesive used.

The improved rheological properties of the composition according to the invention may render it easily possible to process the adhesive by methods such as injection moulding or vacuum moulding.

In one embodiment of the invention the composition may be in the form of a foam.

The combination of improved rheological and cohesive properties of microcolloid adhesives creates the opportunity of producing stable, yet moisture absorbent and transmitting, porous or foamed adhesives. Foamed adhesives are especially interesting as they may provide improved cost, improved moisture handling properties, improved adhesion to flexible and/or uneven substrates and potentially improved skin compatibility.

The foamed adhesive may be characterised by porosity, stability, open/closed or mixed cell structure and cell size distribution. The higher porosity, the softer and more flexible an adhesive is produced with minimal base adhesive consumption. It is preferred that the porosity is between 10 and 80%, and more preferred between 40 and 70%. Open cells will yield a higher moisture absorption and transmission rate. Closed cells will provide the best physical stability. Foamed adhesive with small sized cells may be preferred.

The foamed adhesive may be produced by mechanical introduction and dispersion of a suitable expanding moiety, e.g. compressed air, nitrogen, carbon dioxide, argon or other gasses or low boiling point liquids. Suitable equipment may include the "FoamMelt®" and "FoamMix®" machines available from the Nordson Corporation.

The foamed adhesive may alternatively be produced by compounding the adhesive with a suitable chemical blowing agent, which may generate gas bubbles by a variety of mechanisms. These mechanisms include, but are not limited to chemical reaction, thermal decomposition or chemical degradation, volatilisation of low boiling materials, expansion of gas filled materials or by a combination of these methods.

The term chemical blowing agent is used herein to cover the use of single or multiple component chemicals in a mixture or paste. Suitable chemical blowing agents include the carbonates of alkali metals, such as ammonium carbonate, ammonium bicarbonate, sodium carbonate, sodium bicarbonate, and calcium carbonate. Improved gas generation may be obtained by preparing a mixture of carbonates of alkali metals and various organic acids. Other suitable blowing agents includes expanding spheres such as "Expancel®" available from Akzo Nobel.

The foamed adhesive may be coated or otherwise shaped by a wide number of possible processes including reverse roll coating, slot die coating and different moulding techniques such as injection and vacuum moulding. The foamed adhesive may by further shaped by e.g. cutting or bevelling and it may be laminated onto other materials. The foamed adhesive may be coated into thin layers, as well as it may be moulded into three-dimensional structures.

A medical device according to the invention is typically in the form of a laminate comprising a backing layer, a layer of adhesive and which optionally is covered in part or fully by one or more release liners or cover films to be removed before use. The device may further comprise a secondary backing layer to be removed before use.

In one embodiment of the invention the polymeric matrix is a soft and mouldable paste. Such paste may be useful e.g. for sealings around a stoma or filling agent for wounds.

The adhesive composition may be placed on a backing layer.

The backing layer of the device according to the invention may be any layer, such as a polyurethane film, foam or non-wowen or combination of films or layers which, in combination with the adhesive, shows the desired characteristics of the device according to the invention. The film may e.g. be produced from a polyolefinic material, PVAl, polyester, polyamid, silicones, Teflon®, polyurethane material or polyethylene or copolymers or blends thereof.

The film may be biodegradable or solubilised under certain conditions.

A preferred material for the backing layer may be polyurethane in the form of a film or a foam or combinations of such e.g. in the form of laminates.

The skin-contacting surface of the device may be covered by one or more release liners.

Release liners which are especially suitable for use with the device of the invention can be made of kraft papers, polyethylene, polypropylene, polyester or composites of any of these materials. The liners are preferably coated with release agents such as fluorochemicals or silicones. The release liner may, if present, be removed before, during, or after application. If only removed after application, the release liner may act as a handle during application.

The adhesive layer may be in the form of a continuous layer or a pattern or the adhesive may only be situated on a part of the skin-facing side of the device, e.g. on a flange around the central part of the device to form an island dressing with a non-adhesive or low-adhesive absorbent pad at the central part of the dressing.

The adhesive composition may be in the form of an absorbent pad.

The medical device according to the invention may e.g. be a wound care device, continence device, breastcare device, an ostomy appliance or any adhesive device for application to the skin.

The medical device of the invention may be a dermatological dressing.

The medical device may be a sealing paste for ostomy.

The medical device may be an ostomy appliance.

The medical device may be in the form of a spray, e.g. for use as a primer coating on contoured areas or for breathable and conformable spray adhesives.

The invention further relates to a process for preparing an adhesive composition comprising a polymeric matrix and microcolloid particles wherein the microcolloid particles are dispersed in one of the components of the polymeric matrix before combining further with the rest of the components of the polymeric matrix.

The microcolloid particles may be incorporated into the polymeric matrix in the form of a paste or a liquid dispersion. The dispersing liquid may optionally be removed subsequently.

The microcolloid particles may be incorporated in the form of agglomerates or granules which are broken down before or during the adhesive manufacturing process.

The microcolloid may be in a stabilised form, preferably as a dispersion.

In one embodiment of the invention the composition may be foamed by mechanically introducing an expanding moiety into the composition.

In another embodiment of the invention the composition may be foamed by introducing a chemical blowing agent.

The adhesive composition may be produced by hot-melt mixing in continuous or conventional batch processing. In a batch mixing process a premix of the polymeric matrix may be prepared and subsequently the microcolloid particles, suspended in one or more of the matrix components, are dispersed in the polymeric matrix. The microcolloid particles may alternatively be applied in the form of a dispersion in a volatile solvent which solvent may be removed during or after mixing with the other components of the composition or evaporated in-situ when applying the adhesive. Traditional hydrocolloids may be added subsequently in the form of a powder.

Continuous mixing in single or double screw extruders may be used alternatively.

The present invention provides a method of formulating, producing and using adhesives where the addition of moisture regulating microcolloids provides an improved moisture transmission rate compared to state of the art technology and/or where the rheological properties of the adhesive matrix are less affected than by addition of traditional hydrocolloids. Furthermore the invention provides means of producing breathable hydrocolloid adhesives with lower coat weight than present technology.

The adhesive matrix may comprise any suitable adhesive known per se, such as a pressure sensitive adhesive, which is defined by the Pressure Sensitive Tape Council (Glossary of Terms Used in Pressure Sensitive Tape Industry, PSTC, Glenview, I11. 1959) to be adhesives "which in dry form are aggressively and permanently tacky at room temperature and firmly adhere to a variety of dissimilar surfaces upon mere contact without the need of more than finger or hand pressure. "These adhesives" have a sufficiently cohesive holding and elastic nature so that, despite their aggressive tackiness, they can be handled with the fingers and removed from smooth surfaces without leaving a residue. " Because pressure sensitive adhesives vary in their strength and adhesiveness, their selection for use in the composition will depend on the final application desired.

The Microcolloid

Microcolloids are a new group of water absorbent particles for adhesives. Microcolloids are distinguished from hydrocolloids by having a very fine particle size, preferably below 20 µm, more preferably below 10 µm and even more preferably below 6 µm, and most preferred below 2 µm. They often have a predominately spherical geometry.

The microcolloids of the present invention are less suitable to handle in the form of a powder due the dust problems caused by the very fine particle size and hence they are often used in formulated form. This may be as a liquid dispersion, a paste or a meltable block of particles, where the microcolloids are dispersed in one or more of the components of the final adhesive matrix, e.g. plasticisers, low molecular weight polymers, or a tackifying resin. Alternatively the microcolloids may be in the form of a solid or semi solid granulate which is broken down during processing of the adhesive. The microcolloid granulate may further comprise one or more of the adhesive components such as the elastomer, high melting tackifying resin or traditional granulate binders. Or the microcolloids are in the form of a dispersion in a volatile solvent which solvent may be removed during production of the final adhesive composition or device or evaporated in situ when the adhesive is used.

The microcolloids of the present invention may comprise of any type of water soluble or swellable material which can be formulated into ultra-fine particles. Varieties of microcolloids within the scope of the present invention include synthetic polymers prepared from single or multiple monomers, naturally occurring hydrophilic polymers or chemically modified naturally occurring hydrophilic polymers. The hydrocolloid polymers may be linear or crosslinked. This include natural or chemically modified natural polymers like cellulosics such as CMC, chitosan, pectin, guar gum, starches or dextrines, collagenes and gelatine and synthetic polymers like polyacrylic acid, polyvinylealcohol/vacetate, polyhydroxyalkyl acrylates and methacrylates, polyacrylamides, polystyrene sulfonates, polyvinyl pyrilidone, polyglycols, copolymers, grafts of such, copolymers or compositions of such.

The ultra fine particle size may be obtained by physical means; wet milling, sonication, high shear, but preferably the microcolloid particles are produced by some means of an emulsion process to provide very fine spherical particles. One way of producing microcolloids is to emulsify an aqueous solution of the polymer in a hydrophobic liquid and subsequently distilling of the water. Another way is to use the product from an emulsion polymerisation process.

In general it is desirable that the microcolloids is substantially free of volatile components which will evaporate during processing of the adhesive.

It is desirable that the microcolloids is prepared on a stabilised form, which will allow raw material storage, mixing and processing without significant instability.

In a preferred embodiment of the invention the stabilised microcolloids are in the form of a dispersion and stabilised by low-molecular weight surfactants.

The stabilised microcolloid dispersion may further comprise polymeric steric stabilisers in order to secure the desired rheological properties.

It is well know to stabilise and remove volatile components and dehydrate polymer suspensions by distillation, for example as describe in e.g. U.S. Pat. No. 4,052,353. Further stabilisation may be obtained by use of suitable polymeric stabilisers for example as described in U.S. Pat. No. 4,339,371.

The Hydrocolloid

The physical form of hydrocolloids are relatively coarse and irregular, typically particles with a diameter of about 60-100 μm and usually supplied in the form of a dry powder. These hydrocolloids are hence fairly easy to produce by conventional techniques like milling and their coarse size support safe handling in production, by minimising dust formation.

In one embodiment of the invention the adhesive composition comprises both hydrocolloid particles and microcolloid particles. This may be desirable for obtaining some of the good characteristics of the microcolloid adhesive, obtaining synergistic effects, or simply for optimising costs.

Suitable hydrocolloids for incorporation in the adhesive compositions of the invention are selected from naturally occurring hydrocolloids, semisynthetic hydrocolloids and synthetic hydrocolloids. Varieties of hydrocolloids within the scope of the present invention include synthetic polymers prepared from single or multiple monomers, naturally occurring hydrophilic polymers or chemically modified naturally occurring hydrophilic polymers. The hydrocolloid polymers may be linear or cross-linked.

More particularly, the hydrocolloids are preferably selected from guar gum, locust bean gum (LBG), pectin, alginates, gelatine, xanthan and/or gum karaya; cellulose derivatives (e.g. salts of carboxymethylcellulose such as sodium carboxymethylcellulose, methylcellulose and hydroxypropylmethylcellulose) and/or sodium starch glycolate and/or polyvinylalcohol and/or polyethylene glycol, polyhydroxyalkyl acrylates and methacrylates, polyacrylamides, polyacrylic acid, polystyrene sulfonates, natural or synthetically modified polysaccharides, such may be alginates, pectins, xantan gums, guar gum, chitosan, carboxy methyl cellulose and hydroxy ethyl or hydroxypropyl cellulose.

The Pressure Sensitive Adhesive or Paste

In medicinal application, the pressure sensitive adhesive is suitably tacky at room temperature as well as at skin temperature of the user. Also, the adhesive must be dermatologically acceptable, i.e., after continuous contact with skin, there is little or no adhesive residue upon removal and there is no significant reaction with skin during or after adhesion.

The strength of the pressure sensitive adhesive phase of the composition depend on the type of pressure sensitive adhesive chosen. The adhesives must provide sufficient adhesive strength to adhere the microcolloid containing composition of the invention to the skin of the user.

The pressure sensitive adhesive may comprise polymeric adhesive compositions prepared from a combination of monomers, homopolymers, copolymers, A-B-A block copolymers, A-B block copolymers, tackifiers and plasticisers, or blends thereof to produce polymeric adhesive compositions containing polyolefins, polyacrylates, silicone adhesives, natural or synthetically derived rubber based adhesives, or polyvinyl ethers.

Preferably, the pressure sensitive adhesives useful in the composition may be hydrophobic allowing the adhesives of the pressure sensitive adhesive to resist absorbing moisture or other body exudates gathering at the skin or skin opening during use. The composition retains its strong adhesiveness even in the presence of water or exudates since the pressure sensitive adhesive is unaffected and not plasticised by these agents. Excess moisture is taken away from the skin surface by the microcolloids having a high moisture vapour transmission rate. This decreases the risk of adhesion loss due to pooling of moisture on the skin-facing side of the adhesive.

Preferred adhesives are A-B-A block copolymer pressure-sensitive adhesives, such as polystyrene-polybutadiene-polystyrene (S-B-S), polystyrene-polyisoprene-polystyrene (S-I-S), polystyrene-poly(ethylene/butylene)-polystyrene (S-EB-S), and polystyrene-poly(ethylene/propylene)-polystyrene (S-EP-S) polymers. Other useful adhesives are described in the literature. In the Handbook of Pressure Sensitive Adhesive Technology 2nd Ed., Satas, Editor, (Von Nostrand Reinhold, New York 1989), a number of types of useful pressure sensitive adhesives are discussed: A-B-A block copolymer adhesives, amorphous poly alpha olefins, natural rubbers, polyisoprene, butyl rubber, polyisobutylene, silicones, polychloroprene, acrylic adhesives and acrylic dispersions and polyvinylethers. Any of these pressure sensitive adhesives, or blends thereof, may be used to form the polymeric matrix into which the microcolloids may be dispersed.

The polymeric matrix may further comprise tackifiers, A-B block copolymers, low molar weight rubber, plasticisers etc. or blends thereof in order to adjust the elastic and coherent properties of the polymeric matrix.

The polymeric matrix of the sealing or absorption paste may be polymeric compositions prepared from a combination of polyolefines in molecular weights enabling the mouldable nature into which the hydrocolloids and microcolloids according to the invention are embedded in levels of typically 10 to 60 percent by weight. An alternative composition may be based on the block copolymers of the A-B-A nature described in association with the adhesives.

The polymeric matrix of the absorbent may be any continues phase of soft and expandable type. Preferred are rubber or elastomeric types and most preferred are types derived from the block copolymers.

Alternatively may compositions in which moisture may lead to softening of the structure be applicable. Examples may be acrylics, polyvinyl pyrrolidone, polyvinyl alcohol or acetate, polyethylen glycol, copolymers or blends comprising such.

Optional Components

In some aspects of the invention it may be desirable to prepare the pressure sensitive adhesive composition of the invention with other solids, e.g. non absorbing particles or pigments. E.g. a combination of microcolloids and more coarse and/or irregular particles may be useful to formulate a high module pressure sensitive adhesive or pastes with moisture absorption and transmission rates above the level obtainable by traditional methods.

The addition of a variety of biologically active materials into the microcolloid composition of the present invention may be desirable. The microcolloid compositions may be used for a tailor-fit controlled release of both hydrophobic materials, typically released through the hydrophobic polymer matrix or hydrophilic components typically released through the microcolloid phase.

Hence, the composition of the invention may comprise one or more pharmaceutically or biologically active ingredients.

The adhesive composition according to the invention may comprise wound healing associated indicator(s) such as indicators of pH, partial pressure of $O_2$, temperature, radical mechanisms or biotechnological assays, e.g. indicating formation of collagen.

It is also advantageous that a medical device according to the invention comprises wound healing associated indicator(s), cushions or similar device for treatment or prophylaxis of formation of wounds and/or skin abnormalities.

This opens for a combined medical treatment of a wound or skin and an easy and sterile application of the active ingredients, e.g. by incorporating active ingredients such as a cytokine such as growth hormone or a polypeptide growth factor giving rise to the incorporation of such active substances in a form being apt to local application in a wound in which the medicament may exercise its effect on the wound, other medicaments such as bacteriostatic or bactericidal compounds, e.g. iodine, iodopovidone complexes, chloramine, chlorohexidine, silver salts such as sulphadiazine, silver nitrate, silver acetate, silver lactate, silver sulphate, silver-sodium-thiosulphate or silver chloride, silver-complexes, zinc or salts thereof, metronidazol, sulpha drugs, and penicillins, tissue-healing enhancing agents, e.g. RGD tripeptides and the like, proteins, amino acids such as taurine, vitamins such as ascorbic acid, D-vitamine derivatives, enzymes for cleansing of wounds, e.g. pepsin, trypsin and the like, proteinase inhibitors or metalloproteinase inhibitors such as Illostat or ethylene diamine tetraacetic acid, cytotoxic agents and proliferation inhibitors for use in for example surgical insertion of the product in cancer tissue and/or other therapeutic agents which optionally may be used for topical application, antioxidants, fungicides, nicotine, nitroglycerine, antiinflamatory drugs, NSAIDS such as ibuprofen, ketoprofen or diclofenac, cortico steroids, pain relieving agents such as lidocaine or chinchocaine, emollients, retinoids or agents having a cooling effect which is also considered an aspect of the invention.

EXAMPLES

Example 1

Microcolloids were obtained from Ciba Specialty Chemicals in the form of "Collafix PP80" which is a 50% w/w dispersion of particles with a size of about 0.5-1 µm cross-linked polyacrylic acid based copolymer which intended use was as "Prepaste adhesive for wallpaper".

acResin A 258, UV-curable acrylic adhesive (BASF)
Collafix PP80, 50% w/w microcolloids, Carrier oil: Aliphatic hydrocarbon. Ciba
Specialty Chemicals
PU Backing film, Moisture Permeable (MTR app.12-13.000 $g/m^2/24$ hours)

1 part acResin A258 was mixed on a standard laboratory mixer with 2 parts Collafix PP80. The carrier oil was removed by placing the mixture in a vacuum oven over night, producing a acResin:microcolloid mix of approximately 1:1, Mixture A 1 part of A was mixed with 4 parts of ethanol to produce solution B and 1 part acResin was dissolved in ethanol to produce solution C.

Solution B & C were mixed to produce a range of microcolloid dosages, coated on the PU backing by means of standard bar coating to produce a solvent coat of about 100 µm (wet) resulting in a dry adhesive coat of about 20 µm. The adhesive was cured by UV radiation after the ethanol had been allowed to evaporate. Moisture transmission and peel was measured, and the results are shown in Table 1.

TABLE 1

| | 20 µm acResin/Collafix on PU | | | | | | | | | |
|---|---|---|---|---|---|---|---|---|---|---|
| Sample | 1.1 | 1.2 | 1.3 | 1.4 | 1.5 | 1.6 | 1.7 | 1.8 | 1.9 | 0* |
| % Microcolloids | 0 | 2 | 4 | 7 | 10 | 15 | 22 | 33 | 50 | |
| Peel from steel (N/20 mm) 23° C. | 7.5 | 6 | 6.2 | 5.6 | 5.8 | 3.8 | 3.2 | 2 | 1.3 | |
| Transmission** (kg/m2/24 hours) | 2 | 2.8 | 2.7 | 2.7 | 2.9 | 3.4 | 5.2 | 12 | 12 | 13 |

*Backing without adhesive
**Measured in a standard Pattington cup with 0.9% NaCl, 37° C., 15% RH Major moisture transmission improvements are obtained by addition of microcolloids to the adhesive matrix and it is possible to prepare very thin transmitting coatings of adhesive.

The adhesive may be modified by standard techniques, e.g. addition of softeners or resins to adjust the adhesive properties.

Example 2

Microcolloids were obtained from Ciba Specialty Chemicals in the form of Salcare SC91 but without the activating surfactant and as a 60% w/w dispersion of 0.5-1 µm cross-linked polyacrylic acid based copolymer particles, which intended use was as rheology modifier for personal care products.

Salcare SC91, w/o activating surf., 60% Solids, microcolloids, Ciba Specialty Chemicals
Kraton 1107CU, Styrene-lsoprene-Styrene polymer, Shell
Arkon P115, Tackifying resin, Arakawa Chemical Industries, LTD
Parafluid PL500, white mineral oil, PARAFLUID Mineraloelgesellschaft mbH
Aquasorb A500, Hydrocolloid, Crosslinked CMC, Aqualon
PU Backing film, Moisture Permeable (MTR app.12-13.000 g/m2/24 hours)

The microcolloids were neutralised by addition of 5M NaOH to the dispersion until the solution pH where above 9 in order to maximise swelling, and water was removed by vacuum distillation.

2 parts of the neutralised microcolloids were diluted with 1 part petroleum spirit (60-80° C. Bp) to make up Solution D 1 part Kraton 1107 was dissolved in 9 parts petroleum spirit (60-80° C. Bp) to make up Solution E 1 part Arkon P115 was dissolved in 1 part petroleum spirit (60-80° Bp) to make up Solution F Solutions D, E, F, parafluid PL500 and Aquasorb A500 were mixed according to Table 2 below, coated onto siliconised paper frames and the petroleum spirit was allowed to evaporate.

TABLE 2

| | % w/w Solids | | |
|---|---|---|---|
| | Adhesive A1 | Adhesive A2 | Adhesive A3 |
| Kraton 1107 | 15% | 15% | 24% (15 parts) |
| Arkon P115 | 22.5% | 22.5% | 36% (22.5 parts) |
| Mineral oil | 25%* | 25%** | 40%** (25 parts) |
| Microcolloid | 37.5% | 0% | 0% |
| Aquasorb A500 | 0% | 37.5% | 0% |
| Total | 100% | 100% | 100% |

*From the microcolloid dispersion
**Parafluid PL500

The three adhesives A1, A2 and A3 have the same polymeric matrix and differs only in dispersed phase, so A1 is the microcolloid adhesive, A2 is the traditional hydrocolloid adhesive and A3 is the control without dispersed phase.

The dried adhesives were removed from the paper frame and warm pressed to 200 µm thickness and laminated onto the permeable PU backing.

The following parameters were measured: Absorption speed, absorption capacity, moisture vapour transmission rate, peel, adhesive tack (1 mm adhesive, no backing) and rheological properties (1 mm adhesive, no backing). The methods and results are shown below.

Absorption Speed:

Absorption speed was measured by mounting a 2½×2½ cm sample of adhesive on a small glass slide, submersing the adhesive in a 0.9% NaCl solution and measuring the weight gain as function of time. The results are shown in Table 3.

TABLE 3

Absorption speed, after 30 min. in 0.9% NaCl, 37° C.

| Adhesive | Absorption speed |
|---|---|
| A1) Microcolloid adhesive | 98000 g/m$^2$/24 hours |
| A2) Hydrocolloid control | 19000 g/m$^2$/24 hours |
| A3) No dispersed phase control | 1000 g/m$^2$/24 hours |

As shown in Table 3 the microcolloid adhesive provides superior initial absorption, which is desired, e.g. in order to get good and fast adhesion to wet or moist surfaces.

Absorption Capacity:

Absorption capacity is measured in the same way as absorption speed, only after longer time. Apart the actual weight gain, the cohesion of the swelled adhesive is important in order to render it possible to remove the adhesive without leaving residues. The results are shown in Table 4.

TABLE 4

Absorption capacity, w/w, after 24 hours in 0.9% NaCl, 37° C.

| Adhesive | Absorption capacity | Character |
|---|---|---|
| A1) Microcolloid adhesive | 1740%, | Good cohesion |
| A2) Hydrocolloid control | 800%, | Poor-fair cohesion |
| A3) No dispersed phase control | 20% | Very good cohesion |

As can be seen from the table, this type of microcolloids provide a high swelling capacity, and most importantly combined with good cohesion.

Moisture Transmission:

Moisture transmission is measured by an inverted Pattington cup method.

The moisture vapour transmission is measured as g/m2/24 hours in 0.9% NaCl, 37° C., 15%RH. The results are shown in FIG. 1.

As disclosed in FIG. 1 the microcolloid adhesive does not only provide higher moisture transmission, 12-13000 g/m2/24 hours (same as backing), compared to about 5000 g/m2/24 hours for the hydrocolloid control, but also the lack time before maximum transmission is reached is much shorter.

Peel

Peel adhesion is measured as 90° peel from steel plates, at 23° C., 50% RH, 304 mm/min, 25 mm., Instron model 5564 tensile tester (PSTC-2). The results are shown in Table 5.

TABLE 5

| Adhesive | Peel adhesion |
|---|---|
| A1) Microcolloid adhesive | 14.2 N |
| A2) Hydrocolloid control | 0.9 N |

As can be seen from the table, the peel adhesion of the microcolloid adhesive is much higher than that of the hydrocolloid control.

Adhesive Tack

The adhesive tack is measured as probe tack with a 5 mm teflon probe, at 23° C., 50% RH. (Instron model 5564 tensile tester). The results are shown below in Table 6.

TABLE 6

| Adhesive | Adhesive tack |
|---|---|
| A1) Microcolloid adhesive | 7.8 mJ |
| A2) Hydrocolloid control | 1.2 mJ |

As disclosed in the table, the adhesive tack is much improved when comparing the microcolloid adhesive with the hydrocolloid control.

Example 3

Preparation of Foamed Adhesive with Microcolloids.

MicroColloids DP199-9086 were obtained from Ciba Specialty Chemicals, as a 55% w/w dispersion of 0.5-1 µm cross-linked poly acrylic acid based copolymer particles.
DP199-9086, 55% Solids, Ciba Specialty Chemicals
Quintac 3433N, Styrene-lsoprene-Styrene polymer, Nippon Zeon Ltd.

Arkon P115, Tackifying resin, Arakawa Chemical Industries, LTD

PU Backing film, Moisture Permeable (MTR app.12-13.000 g/m2/24 hours)

The adhesive was hot melt processed in a Herman Linden z-blade mixer (Machine type LK 110.5) with an circulating oil temperature at 160° C.

The ingredients of Table 7 were mixed:

TABLE 7

| Quintac 3433N | 100 parts w/w |
| Arkon P125 | 112 parts w/w |
| DP199-9086 | 122 parts w/w |

After the processing of the adhesive the bulk adhesive was placed in a FoamMelt 130 from Nordson, which is designed to force gas (in this case inert Nitrogen) into dispersion in the moulded adhesive.

The temperature in the chamber, where the adhesive was melted, was 170 degree C. After the adhesive was melted the density controller was adjusted. After 20 min. of circulation the density was constant and the foamed adhesive were dispensed onto a siliconised paper. Just after application the gas expands to create a closed-cell foam. A soft and stable foam with excellent adhesive properties was obtained.

The foamed adhesive was laminated on to a PU backing. The thickness of the foam layer was: 0.3 mm, 0.6 mm, 1.0 mm and 2.0 mm.

Compared to unfoamed adhesives, the foamed adhesive was provided the following benefits:
increased adhesion to flexible substrates
increased flexibility
lower pain upon removal from the skin
improved soft feel
reduced adhesive consumption The porosity of the 2.0 mm foamed adhesive was determined immediately after preparation and again after 2 weeks stored at 40 degrees C. The results are shown in Table 8.

TABLE 8

| Initial porosity | Porosity after 2 weeks |
| --- | --- |
| 47.3% | 46.9% |

The results of Table 8 show a very good stability of the foamed adhesive.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

The invention claimed is:

1. An adhesive composition comprising a polymeric matrix and absorbent particles, wherein 100% w/w of the absorbent particles being microcolloid particles having a substantially rounded or spherical shape with at least 90% of said microcolloid particles having a size of less than 1 micron.

2. The composition according to claim 1, wherein the microcolloid particles are delivered in a carrier liquid in a stabilized form through presence of low-molecular weight surfactants.

3. The composition according to claim 1, wherein the composition is in the form of a foam.

4. The composition according to claim 1, wherein the composition is a medical adhesive.

* * * * *